US008025803B2

(12) United States Patent
Bridey et al.

(10) Patent No.: US 8,025,803 B2
(45) Date of Patent: Sep. 27, 2011

(54) USE OF A CHROMATOGRAPHY SUBSTRATE FOR REDUCING THE AMOUNT OF ADAMTS13 IN A SOLUTION DERIVED FROM PLASMA

(75) Inventors: Francoise Bridey, La Reine (FR); Roland Schmitthaeusler, Montigny le Bretonneux (FR)

(73) Assignee: LFB Biotechnologies, Les Ulis (FR)

( * ) Notice: Subject to any disclaimer, the term of this patent is extended or adjusted under 35 U.S.C. 154(b) by 0 days.

(21) Appl. No.: 12/667,751

(22) PCT Filed: Jul. 7, 2008

(86) PCT No.: PCT/FR2008/051251
§ 371 (c)(1),
(2), (4) Date: Jan. 5, 2010

(87) PCT Pub. No.: WO2009/007661
PCT Pub. Date: Jan. 15, 2009

(65) Prior Publication Data
US 2010/0193440 A1  Aug. 5, 2010

(30) Foreign Application Priority Data
Jul. 5, 2007 (FR) ...................................... 07 56303

(51) Int. Cl.
*B01D 15/08* (2006.01)
(52) U.S. Cl. .................. 210/635; 210/656; 210/198.2; 530/381; 530/416
(58) Field of Classification Search .................. 210/635, 210/656, 198.2, 502.1; 530/380, 381, 387.9, 530/416
See application file for complete search history.

(56) References Cited

U.S. PATENT DOCUMENTS

| | | | | |
|---|---|---|---|---|
| 4,753,983 A * | 6/1988 | Ngo | | 525/54.1 |
| 7,112,666 B2 * | 9/2006 | Soejima et al. | | 536/23.2 |
| 7,361,748 B2 * | 4/2008 | Soejima et al. | | 536/23.1 |
| 7,517,522 B2 * | 4/2009 | Ginsburg et al. | | 424/94.67 |
| 7,662,946 B2 * | 2/2010 | Ginsburg et al. | | 536/23.2 |
| 7,833,726 B2 * | 11/2010 | Kato et al. | | 435/7.1 |
| 2004/0214275 A1 * | 10/2004 | Soejima et al. | | 435/69.1 |
| 2008/0254527 A1 * | 10/2008 | Soejima et al. | | 435/212 |
| 2010/0193440 A1 * | 8/2010 | Bridey et al. | | 210/656 |
| 2011/0081700 A1 * | 4/2011 | Hasslacher et al. | | 435/174 |

FOREIGN PATENT DOCUMENTS

| | | |
|---|---|---|
| EP | 1 391 516 A | 2/2004 |
| WO | 02/42441 A | 5/2002 |
| WO | 2006/133955 A | 12/2006 |

OTHER PUBLICATIONS

Fujikawa K et al, "Purification of human von Willebrand factor-cleaving protease and its identification as a new member of the metalloproteinase family", Blood, Sep. 15, 2001, pp. 1662-1666, vol. 98, No. 6, W.B.Saunders Company, Orlando, FL, XP002972407.
Furlan M et al, "Partial Purification and Characterization of a Protease From Human Plasma Cleaving von Willibrand Factor to Fragments Produced by in Vivo Proteolysis", Blood, May 15, 1996, pp. 4223-4234, vol. 87, No. 10, W.B. Saunders, Philadelphia, VA, XP002042011.
International Search Report in Corresponding Application No. PCT/FR2008/051251 dated Dec. 23, 2008.

* cited by examiner

*Primary Examiner* — Ernest G Therkorn
(74) *Attorney, Agent, or Firm* — Young & Thompson (57) ABSTRACT

An ion-exchange chromatography support for reducing the ADAMTS13 amount present in a plasma-derived solution containing human von Willebrand factor. The support includes a large-pore, vinyl polymer-type resin bearing DEAE groups, and a buffer including trisodium citrate, sodium chloride, calcium chloride, glycine and lysine.

8 Claims, 6 Drawing Sheets

Figure 1

Figure 1 (Suite 1)

Figure 1 (Suite 2)

Figure 2

Figure 2 (Suite 1)

Figure 2 (Suite 2)

USE OF A CHROMATOGRAPHY SUBSTRATE FOR REDUCING THE AMOUNT OF ADAMTS13 IN A SOLUTION DERIVED FROM PLASMA

REFERENCE TO RELATED APPLICATIONS

This application is a 371 of PCT/FR08/51251 filed Jul. 7, 2008.

FIELD OF THE INVENTION

The field of this invention relates to the purification of proteins. The present invention relates, in particular, to a method for reducing the amount of the ADAMTS13 protein present in von Willebrand factor (vWF) solution and to the use of chromatography supports and of specific buffers for reducing the amount of the ADAMTS13 protein present in such samples.

PREVIOUS ART

The von Willebrand factor (vWF) is the largest molecule ever known which circulates in blood plasma. vWF consists of a plurality of multimers bound through disulfide bridges, the base structural element of which has a molecular weight of about 250 kilodaltons (KDa). The smallest vWF form, in plasma, is a dimer of 500 KDa and the biggest forms are multimers of this dimer, the molecular weight of which can reach up to 20 millions daltons. Such arrangement of the subunits to multimers may be specific of producing cells, vWF being synthesized and polymerized in megakaryocytes and in endothelial cells.

This factor plays a crucial role in haemostasis through two different functions: on the one hand, as an adhesion protein, it enables the blood platelets to adhere and to aggregate to the vascular subendothelium (and thus takes part to the primary haemostasis process that does occur in the damaged vessels) and, on the other hand, it ensures Factor VIII (FVIII) stabilization and transport in blood circulation.

A vWF congenital deficiency (quantitative deficiency) or a structural anomaly of this factor (qualitative deficiency) leads to von Willebrand disease which does manifest itself by skin-mucosal bleedings. This disease has a very heterogeneous clinical expression and is very problematic in case of surgical operations. Treating the von Willebrand disease is incontrovertible for correcting anomalies of the primary haemostasis (bleeding time) and of the coagulation (activated partial thromboplastin time and clotting activity of FVIII, FVIII: C).

The disease is treated by a substitution therapy using vWF-enriched human plasma derivatives (for example the cryoprecipitated fraction of plasma, FVIII concentrates with a sufficient vWF content (FVIII/vWF concentrate) or vWF concentrates (without FVIII).

The von Willebrand disease may be accompanied, or not, by a FVIII deficiency depending on whether the protein is absent or qualitatively abnormal, respectively. Generally, patients suffering from a deficiency of these both clotting factors are treated with a FVIII/vWF concentrate. By contrast, when the vWF-deficient patient does normally express FVIII, it is preferable to use a vWF concentrate without FVIII. For these patients, the use of such concentrate enables to compensate only the vWF-deficiency and to avoid FVIII excess. FVIII excesses may cause serious complications such as venous thrombosis or pulmonary embolism.

However, vWF concentrates are generally very unstable in solution if vWF is denatured by proteolytic enzymes such as ADAMTS13.

ADAMTS13 is a protease of the metalloprotease family which naturally occurs in human plasma. Its function is to convert the hyperactive long multimers of vWF to smaller less active multimers. ADAMTS 13 is capable of denaturing vWF in vivo but also in vitro, for example in solutions derived from vWF-containing plasma, like vWF concentrates or FVIII/vWF concentrates. While these plasma derivatives may be generally stored as a freeze-dried powder for many years, the fact that ADAMTS13 is present does alter the vWF stability when the freeze-dried powder is dissolved. This problem of vWF stability does exclude some therapeutic treatment forms, for example the continuous or discontinuous infusion treatment for several days. Such treatment enables to maintain constant circulating levels of vWF and thus to prevent the occurring of the levels outside the therapeutic window when the administration is performed by a discontinuous injection.

The applicant therefore aimed to develop efficient means for reducing the amount of ADAMTS13 protein present in compositions derived from vWF-containing plasma, so as to improve over time the stability properties thereof.

SUMMARY OF THE INVENTION

The object of the present invention relates to the use of an ion-exchange chromatography support comprising a large-pore, vinyl polymer-type resin bearing DEAE groups, and a buffer comprising trisodium citrate, sodium chloride, calcium chloride, glycine and lysine, in order to reduce the ADAMTS13 amount in a solution derived from human vWF- and ADAMTS13-containing plasma.

It is a further object of the present invention to provide a method for reducing the ADAMTS13 amount in a solution derived from human vWF-containing plasma comprising an ion-exchange chromatography step on a large-pore, vinyl polymer-type resin bearing DEAE groups performed in a buffer comprising trisodium citrate, sodium chloride, calcium chloride, glycine and lysine.

DESCRIPTION OF THE FIGURES

FIG. 1 shows a diagram of the vWF:RCo concentration vs. time in a vWF concentrate without ADAMTS13 stored in cassettes or syringes.

FIG. 2 shows a diagram of the vWF:Ag concentration vs. time in a vWF concentrate without ADAMTS13 stored in cassettes or syringes.

DESCRIPTION OF THE INVENTION

The applicant surprisingly discovered that some types of ion-exchange chromatography supports used under specific conditions are able to remove ADAMTS13 protein molecules, or to efficiently reduce the amount of ADAMTS13 protein, which is present in vWF-enriched compositions.

Thus, the present invention relates to the use of an ion-exchange chromatography support comprising a large-pore, vinyl polymer-type resin bearing DEAE groups (diethyl aminoethyl) and a buffer comprising trisodium citrate, sodium chloride, calcium chloride, glycine and lysine, in order to reduce the ADAMTS13 amount present in a solution derived from human vWF-containing plasma.

The present invention further relates to a method for reducing the ADAMTS13 amount in a solution derived from human vWF-containing plasma comprising an ion-exchange chromatography step on a large-pore, vinyl polymer-type resin bearing DEAE groups performed in a buffer comprising trisodium citrate, sodium chloride, calcium chloride, glycine and lysine.

Advantageously, the ion-exchange chromatography support is a DEAE-Fractogel® TSK 650 resin (also called DEAE-Toyopearl 650) equilibrated with a equilibration buffer comprising trisodium citrate 0.01 M, sodium chloride 0.11 M, calcium chloride 0.001 M, glycine 0.12 M and lysine 0.016 M, at pH 7±0.1.

DEAE-Fractogel® TSK 650 is a synthetic hydrophilic gel. The support is a copolymer of oligoethylene glycol, glycidine methacrylate and pentaerythritol dimethacrylate on which DEAE groups such as —O—$CH_2$—$CH_2N^+(C_2H_5)_2$ HCl, are grafted, which results in a weakly alkaline anion exchanger. DEAE-Fractogel® TSK 650 is available in two particle sizes (after re-hydration): type S (0.025-0.050 mm) and type M (0.045-0.090 mm); these both types can be used in the present invention.

According to the present invention, the solutions derived from plasma include blood plasma derivatives, such as the cryoprecipitated fraction (i.e. non purified fraction) and purified derivatives of the cryoprecipitate. The present invention especially relates to solutions derived from plasma that may contain vWF.

In a preferred embodiment, the pre-purified cryoprecipitated fraction of plasma, which has been optionally submitted to a viral inactivation treatment, is introduced into the equilibrated ion-exchange chromatographic column. The retained fraction is then eluted by increasing the sodium chloride concentration in the buffer to 0.14-0.15 M. This step enables to reduce the ADAMTS13 amount more than 500 times as compared to the ADAMTS13 amount initially present in the initial plasma sample (table 1).

In a particular embodiment, the amount of ADAMTS13 present in a plasma-derived solution comprising the von Willebrand factor is reduced by performing two successive ion-exchange chromatography steps, under the conditions as described above, especially with the equilibration buffer as described above.

According to the hereabove mentioned embodiment, the eluted fraction obtained after the use of the first column may be introduced again into a second chromatographic column that is identical to the first one, under the same conditions as those of the first column, except that after removing the filtrate and rinsing the column with the equilibration buffer, the proteins adsorbed onto the chromatography support are eluted by increasing the sodium chloride concentration in the buffer to 0.15-0.17 M. This additional chromatography enables to reduce the amount of ADAMST13 more than 2000 times as compared to the initial ADAMTS13 amount present in the initial plasma sample (table 1).

According to the invention, the reduction of the ADAMTS13 amount is higher than 200 times, 300 times, 400 times, 500 times, 600 times, preferably higher than 700 times, 800 times, 900 times, 1000 times, 1500 times, 2000 times, 2500 times as compared to the ADAMTS13 amount present in the initial plasma sample.

For making a vWF-enriched composition, the fraction, eluted from the ion-exchange chromatography support or from the ion-exchange chromatography support used in a second step, according to the relevant embodiment of the present invention, may then be submitted to an affinity chromatography step on a gelatin-sepharose support, in the presence of a equilibration buffer similar to the equilibration buffer used for performing the ion-exchange chromatography step(s). The gelatin-sepharose chromatography support is able to retain the residual contaminating fibronectin molecules. The choice of the gel support type to be associated with gelatin is not an essential characteristic for carrying out this later chromatography step. The affinity chromatography support may also be suitably selected from gelatin-Ultrogel®, gelatin-Spherodex® and gelatin-Fractogel®. A gelatin-Sepharose® support will be preferably used.

In vitro tests did confirm the stability of the thus obtained vWF-containing concentrate when said concentrate is dissolved (example 3).

By implementing the method for reducing the amount of the ADAMTS13 protein according to the present invention, compositions with a reduced amount of the ADAMTS13 protein and which are enriched with vWF are obtained from various plasma-derived solutions, especially from human plasma. Such compositions, due to the stability properties of the vWF over time, are utilizable in a liquid form for performing medical treatments by intravenously administration of vWF.

The present invention also relates to the use of a liquid composition having a reduced ADAMTS13 protein content and enriched with vWF, such as obtained by the method as defined in the present description, in order to make a drug for preventing or treating a disease associated with a biologically active vWF-deficiency. Advantageously, said drug is in a form suitable for being intravenously administrated. In some embodiments, said drug is in a freeze-dried form, to which a suitable amount of sterile and pyrogen-free water is added so as to make a liquid composition suitable for an intravenous administration. In other embodiments, said drug is in a liquid form which may be directly used for intravenous administration.

The present invention further relates to a method for preventing or treating a disease associated with a biologically active vWF-deficiency, characterized in that it comprises a step wherein a vWF-enriched and ADAMTS13 protein-depleted composition, such as obtained according to the method as defined in the present description is administered to a patient in need thereof.

Advantageously, according to the hereabove treatment or prevention method, the composition administration step consists in an intravenous administration step. Preferably, the intravenous administration step consists in a continuous infusion step, that is to say a continuous infusion step for a time period of at least 8 hours and up to 200 hours, the duration of this step being adapted to the condition of the patient.

The step of continuous-infusion administration does generally last 8 hours to 120 hours, and usually up to 24 hours.

In an advantageous embodiment, the step of continuous-infusion administration is performed with a single container or flask filled with a vWF-enriched and ADAMTS13-depleted composition obtained according to the method of the invention. The use of a single container comprising a single composition batch, for the whole duration of the continuous infusion administration step, is made possible thanks to the vWF high stability in the composition.

Therapeutical methods comprising a step of administrating a composition enriched with the von Willebrand factor are known per se in the state of the art. Such methods were described for example by Martinowitz and al. (1997, Transfusion Medicine Review, Vol. 11: 56-63) and Martinowitz and al. (1994, International Daynal of Pediatric Hematology/Oncology, Vol. 1: 471-478).

Generally, the vWF-enriched and ADAMTS13 protein-depleted composition is administered to the patient, by a continuous infusion, so as to administrate to said patient a von Willebrand factor amount ranging from 20 to 200 vWF:RCo IU/kg,/24 h.

The compositions that are used, obtained directly or indirectly with the method of the invention, do advantageously have a vWF content ranging from 10 to 250 IU/ml, for example 100 IU/ml.

The following examples illustrate the embodiments of the invention but should not be construed as limiting the scope thereof.

EXAMPLES

Example 1

Manufacture of a vWF Concentrate Without ADAMTS13

Starting Material.

Blood was collected in the presence of sodium citrate (4%) or an anti-clotting CPD solution (citrate, phosphate, dextrose), and frozen at the latest 6 hours after sampling thereof. Plasma was obtained after centrifuging, and frozen at −60° C. then stored at −35° C. Plasma batches contained from 1800 to 2000 litres and were pooled to batches of 4000 litres for each implementation of the method. For thawing, plasma was placed within a chamber at −7° C. for at least 12 hours to ensure a slow and regular heating-up, then it was thawed in a thermostated chamber at a temperature of 0-2° C., under constant stirring. The cryoprecipitate (which corresponds to about 9 g/litre of plasma) was recovered by cold centrifugation.

After centrifugation, the recovered cryoprecipitate was re-dissolved and adsorbed onto aluminum hydroxide so as to remove the major contaminants, that is to say the components of the prothrombin complex (particularly factor VII), factor XII. The supernatant was then cooled to 15° C. (which removes part of the fibrinogen and of the fibronectin).

Viral Inactivation Treatment.

The FVIII-vWF-containing solution was submitted to a solvent-detergent treatment known for being efficient against lipid envelope virus (Horowitz and al., 1985, Transfusion, 25, 516-522.) and comprising a 8-hour incubation at 25° C. in the presence of 0.3% tri-n-butyl phosphate (TnBP) and 1% Tween 80.

Chromatographic Separation Method

The first chromatography was performed on a DEAE-Fractogel(M) TSK 650 column (Merk). The equilibration buffer contained trisodium citrate (0.01 M), calcium chloride (0.001 M), sodium chloride (0.11 M), glycine (0.12 M) and L-lysine (0, 016 M). vWF, FVIII and fibronectin were retained onto the column; the contaminant proteins (mainly fibrinogen and IgGs) being poorly fixed onto the column, or even not fixed, and the residues of the viral inactivation treatment were removed with several successive washings using the same buffer.

The column was run at a linear flow rate of 100 cm/hour.

The vWF-containing fraction adsorbed onto the column, was eluted by increasing the NaCl concentration in the buffer to 0.15M.

The fraction containing the eluted vWF from this first column was reinjected in a second column, similar to the first one and under similar conditions, after a slight dilution with the equilibration buffer, to adjust the ionic strength of the vWF fraction to an equivalent of 0.11 M chloride sodium.

The vWF-containing fraction adsorbed onto the column was eluted by increasing the NaCl concentration in the buffer to 0.15 M.

The electrophoresis analysis of the eluate revealed the presence of a small contamination by fibronectin and by inter-alpha trypsin inhibitor (ITI).

This second eluate was submitted to a third purification step on a gelatin-Sepharose CL4B column (Pharmacia) equilibrated with the elution buffer of the previous column, to remove fibronectin.

This affinity chromatography gel has a fibronectin retention capacity of >5 mg/ml which makes it possible to reduce this contaminant to undetectable values (<4 mg/l) in the fraction.

The VWF concentrate having no ADAMTS13 was recovered in the filtrate from this last step and could be directly treated and freeze-dried.

The finally obtained filtrate did not require any stabilizer addition.

Example 2

Measurement of the ADAMTS13 Amount Reduction in the vWF Concentrate

The aim of this example is to measure the reduction factor of the ADAMTS13 amount present in a vWF concentrate prepared according to example 1.

Starting Material.

Four fractions corresponding to the solutions/concentrates before and after each chromatography step of example 1 as well as an initial plasma fraction were collected. For each fraction, a sample of 1 mL, respectively labelled A, B, C, D and E, was collected.

A: initial plasma
B: cryoprecipitate between solvent/detergent and the first DEAE chromatography
C: eluate from the first DEAE chromatography
D: eluate from the second DEAE chromatography
E: fraction of the vWF-containing gelatin-Sepharose column ADAMTS13 Protein Assays.

The ADAMTS concentration in each sample was measured with an IMUBIND® ADAMTS13 ELISA kit (from American Diagnostica) using rabbit anti-human ADAMTS13 antibodies.

At the same time, the vWF:RCo concentration was measured (see assay protocol in example 3).

Results

The results of the different assays are given in table 1 hereunder.

TABLE 1

ADAMTS13 protein and vWF assays in the various steps of the method of example 1 and calculation of the ADAMTS13 reduction factor

| Sample (total volume of the fraction) | ADAMTS13 amount in the fraction (µg) | vWF:RCo | ADAMTS/ vWF:RCo | ADAMTS13 reduction factor |
|---|---|---|---|---|
| A (4000 L) | 2 600 000 µg | 5 200 000 IU | 0.5 µg/IU | 1 |
| B (270 L) | 284 040 µg | 2 430 000 IU | 0.1169 µg/IU | 4 |
| C (74 L) | 1258 µg | 1 776 000 IU | 0.0007 µg/IU | 714 |

TABLE 1-continued

ADAMTS13 protein and vWF assays in the various steps of the method of example 1 and calculation of the ADAMTS13 reduction factor

| Sample (total volume of the fraction) | ADAMTS13 amount in the fraction (µg) | vWF:RCo | ADAMTS/ vWF:RCo | ADAMTS13 reduction factor |
|---|---|---|---|---|
| D (11 L) | 308 µg | 1 452 000 IU | 0.0002 µg/IU | 2500 |
| E (16 L) | 272 µg | 1 104 000 IU | 0.0002 µg/IU | 2500 |

NB: the ADAMTS13 reduction factor is calculated by dividing the ADAMTS/vWF:RCo value of the fraction by the ADAMTS/vWF:RCo value of the plasma fraction.

Conclusion

The ADAMTS13 reduction factor after the first chromatography is higher than 700. This reduction factor is of about 2500 after the second chromatography. By contrast, the third chromatography did not allow to reduce the ADAMTS13 amount. This example reveals the high efficiency of the chromatography columns and of the buffers used for removing the ADAMTS13 proteins.

Example 3

Stability of the VWF Concentrate with no ADAMTS13

The aim of this example is to evaluate the biological stability after reconstitution of the vWF freeze-dried concentrate without ADAMTS13, prepared according to example 1 in various containers and under routine conditions when effecting dose fractionation into syringes or batchwise, or when administrating the product by a continuous infusion using an infusion pump.

Material

Tested drugs: Three different vWF concentrate batches were tested:

Batch #1: vWF:RCo 1010 IU/10 ml flask
Batch #2: vWF:RCo 1080 IU/10 ml flask
Batch #3: vWF:RCo: 1000 IU/10 ml flask Infusion Material Used Infusion pump CADD PRIZM™ VIP (SIMS Deltec, Inc, St Paul, Minn., USA)

MEDICATION CASSETTE™ 50 ml reservoirs, in polyvinyl chloride

Delt extension cord for pump with 114 cm/45 in antisiphon valve in polyvinyl chloride 3P Plastipak 10 ml Luer Lock H810LL Syringes in polypropylene Automatic dosing device: the BCS Analyzer (Dade Behring, Marburg GmbH) for ristocetin cofactor activity assay (vWF:Rco) and vWF antigen assay (vWF:Ag).

Ristocetin cofactor activity assay (vWF:Rco)

BC von Willebrand reagent (Dade Behring Marburg GmbH).

NaCl used for the dilution of the samples

Dilution of the samples: "bovine serum" minimum 98%.

The albumin (bovine serum) was previously diluted in a physiological saline solution. (NaCl 0.9%)

VWF antigen assay (vWF:Ag)

VWF reagent: Ag Dade Behring (Dade Behring Marburg GmbH) comprising:

1 flask vWF: Ag diluent for latex reagent 4 ml: solution containing glycine, for the dilution of the latex reagent 1 flask vWF: Ag latex reagent 2 ml: suspension of small polystyrene particles coated with (rabbit) anti-human vWF antibodies 1 flask vWF: Ag buffer 5 ml: glycine buffer Storage after reconstitution: 15 days at +2/+8° C.

Owren Kroller buffer for the dilution of the samples

Dilution of the samples: bovine serum minimum 98%.

The albumin (bovine serum) was previously diluted in a saline solution (NaCl 0.9%).

Multimer Assays

The reagents and the buffers are the following ones:

Buffer TBS 50 mM, pH 7.4
5% skimmed milk=Saturation buffer
0.05% Tween 20=Washing buffer Anti-vWF polyclonal antibodies coupled with alkaline phosphatase 634.0052

Revelation kit—Biorad (stored at −20° C.)

Standard Plasma and Quality Control

Human standard plasma (Dade Behring Marburg GmbH): calibration to comply with the OMS 97/586 standard.

Controls:

VEQ A (Normal control) (Dade Behring Marburg GmbH)
Target values: RCo: 71% (64-79) and Ag: 90% (83-97)

VEQ B (Pathological control) (Dade Behring Marburg GmbH)
Target values: Rco: 22% (17-27) and Ag: 33% (30-35)

Study Technical Conditions

Room temperature: 23±2° C.

Away from light source

Reconstitution under a laminar air flow hood (class A; ISO 5), in a controlled-atmosphere room (Class C; ISO 7). (in compliance with the Good manufacturing practices: special guidelines: Sterile drug production; Official Bulletin N° 2007/1 bis).

Method

Preparation of Samples—Study Technical Conditions

As a whole six preparations were tested: each batch was tested both in a syringe and in a cassette.

The vWF freeze-dried concentrate without ADAMTS13 is a powder to be extemporaneously reconstituted with water for injectable preparations.

Syringes: at T0, the products were reconstituted with the proposed solvent (water for injection) and the material (transfer system provided with a vent having a sterilizing filter and an edge-type filter), then transferred into the syringes under a laminar air flow hood (class A), in a controlled-atmosphere room (Class C). The study was performed under static conditions for 3 days (72 hours), the preparations were stored at room temperature and away from a light source.

Cassettes: at T0, the products were reconstituted under similar conditions as compared to those for the syringes. The first step was performed under static conditions, for 0 to 48 hours. The second step, extending from 48 to 120 hours was performed under dynamic conditions: the pump was activated on day 2 and maintained at a reduced flow rate (0.1 ml/hour) until the end of the study (120$^{th}$ hour). The preparations were stored at room temperature and away from a light source.

Preparation of the Samples:

Sampling for vWF:RCo and vWF:Ag assays was done just after reconstitution (T0), then at:

T12, 24, 36, 48, 60, 72 hours after reconstitution for the syringes

T12, 24, 36, 48, 60, 72, 84, 96, 108, 120 hours after reconstitution for the cassettes.

A sample (250 μl) was collected in triplicate for each point, in numbered and graduated Eppendorf microtubes, then immediately frozen at −80° C.

Sampling for the multimer assays was effected at:
T0, 72 Hours for the syringes
T0, 60, 120 Hours for the cassettes.
The samples were immediately frozen at −80° C.

Standard Plasma and Controls

VEQ A, VEQ B controls and the standard plasma were reconstituted with 1 ml of non cold distilled water, then were allowed to stabilize for 1 hour. For the vWF:RCo activity assay, a standard range was performed on the same day as the assays. Calibration was performed by automatically diluting the standard with the Owren Koller buffer by means of the BCS device. The analysis of the VEQ A and VEQ B controls enabled to validate said calibration. The controls did run once again at the end of the analysis of the samples corresponding to the syringes, then before those corresponding to the cassettes, thus validating a new reconstitution of the platelet reagent. For the von Willebrand antigen assay, the standard range was validated by the analysis of the VEQ A and VEQ B controls.

VWF:Rco Assay

Assay principle: In the presence of ristocetin (antibiotic), vWF present in a sample induces the agglutination of the stabilized platelets contained in the von Willebrand BC reagent. The agglutination process reduces the turbidity of the reaction mixture. The clotting analyzer (Dade Behring BCS) measures the modification of the optical density and automatically calculates the ristocetin cofactor activity in the sample as a percent related to the normal. A six-point range was set up from the standard plasma from 10 to 150% (10, 20, 40, 60, 100 and 150%).

Method: the vWF BC reagent comprises stabilized platelets, ristocetin and EDTA, in a freeze-dried form. After reconstitution with 4 ml of distilled water, the von Willebrand BC reagent is allowed to stabilize without stirring for 15 minutes. It is then stirred twice very slowly for 5 seconds using a vortex, then is introduced into the BCS device. The latter should be stirred every 30 minutes. NaCl, which is used for the dilution of the samples, is also introduced into the BCS device.

VWF:Ag Assay

Assay principle: the addition of a reagent to a sample which contains the von Willebrand antigen induces the agglutination of the small polystyrene particles coated with covalently-bound specific antibodies (rabbit Ab).

This agglutination is measured by a turbidimetric analysis on the BCS device. Said turbidimetric analysis is directly proportional to the vWF Ag level in the sample. A five-point range was set up from the standard plasma from 10% to 180% (10, 40, 70, 150 and 180%).

Method: the whole diluent flask was poured into the latex reagent flask, then placed under stirring while avoiding bubble formation. After 15 min of rest at room temperature, the mixture was introduced into the automatic device.

Sample Treatment

The samples were thawed for 5 min at 37° C., then stirred with vortex and lastly diluted to 1/100th in bovine serum, minimum 98% (previously diluted in a physiological saline solution). After stirring with vortex, the samples were introduced into the BCS device.

Multimers

Preparation of the samples: the samples were diluted to 1/10th in a sample dilution buffer+bromophenol blue so as to adjust the vWF:Ag level to about 0.1 IU/ml. The samples were then heated for 30 minutes at 60° C.

Electrophoresis: 30 μL of samples were introduced into agarose gel wells. As soon as the electrophoresis was stopped, the gel was dipped in a beaker of distilled water and rinsed for at least 1 hour under mild stirring. The gel was then dried under a cold air flow, then was brought to saturation for 1 hour in a saturation buffer. The gel was incubated overnight, under mild stirring, in a bath of polyclonal anti-vWF antibodies linked to alkaline phosphatase (anti-vWF-PA) diluted in 50 mM TBS buffer. After incubation, the gel was incubated under stirring with several successive washing buffer bathes for at least 2 hours. The revelation solution was prepared by adding to 100 ml of Tris 0.1 M pH 9.5, 1 ml of solution A+1 ml of solution B (kit solutions).

Expression and Results

Exploitation of the results for vWF:Rco and vWF:Ag: a linear regression method was used for the statistical analysis corresponding to a zero order reaction, i.e. the most simple: $y=a+bx$. It was checked that there was no significant difference between slopes by the Student test, with t 0.05 for N-2 dd.

Exploitation of the multimer results: each plate was scanned to obtain a densitometric plot of the bands corresponding to the various multimers. For each band, integration was expressed as a percent of the total area. The bands were identified from 1 to X, from the lightest to the heaviest.

The results are given in percents as related to the totality of:
multimers from the $15^{th}$ band incl. to the Xth band ($\geq$15-mers)
multimers from the 10th band incl. to the Xth band ($\geq$10-mers)
multimers from the 5th band incl. to the Xth band ($\geq$5-mers)

Results

Control Results: Data not Shown

Assay Results

After reconstitution with 10 ml of water for injectable preparation, a flask contained 1000 IU human von Willebrand factor which corresponds to a ristocetin cofactor activity of 100 UI/ml. This study was carried out in compliance with the FDA (Q1D) and EMEA (CPMP/ICH/420/02) recommendations as to the way to evaluate the stability of drugs after reconstitution.

Figure 1:
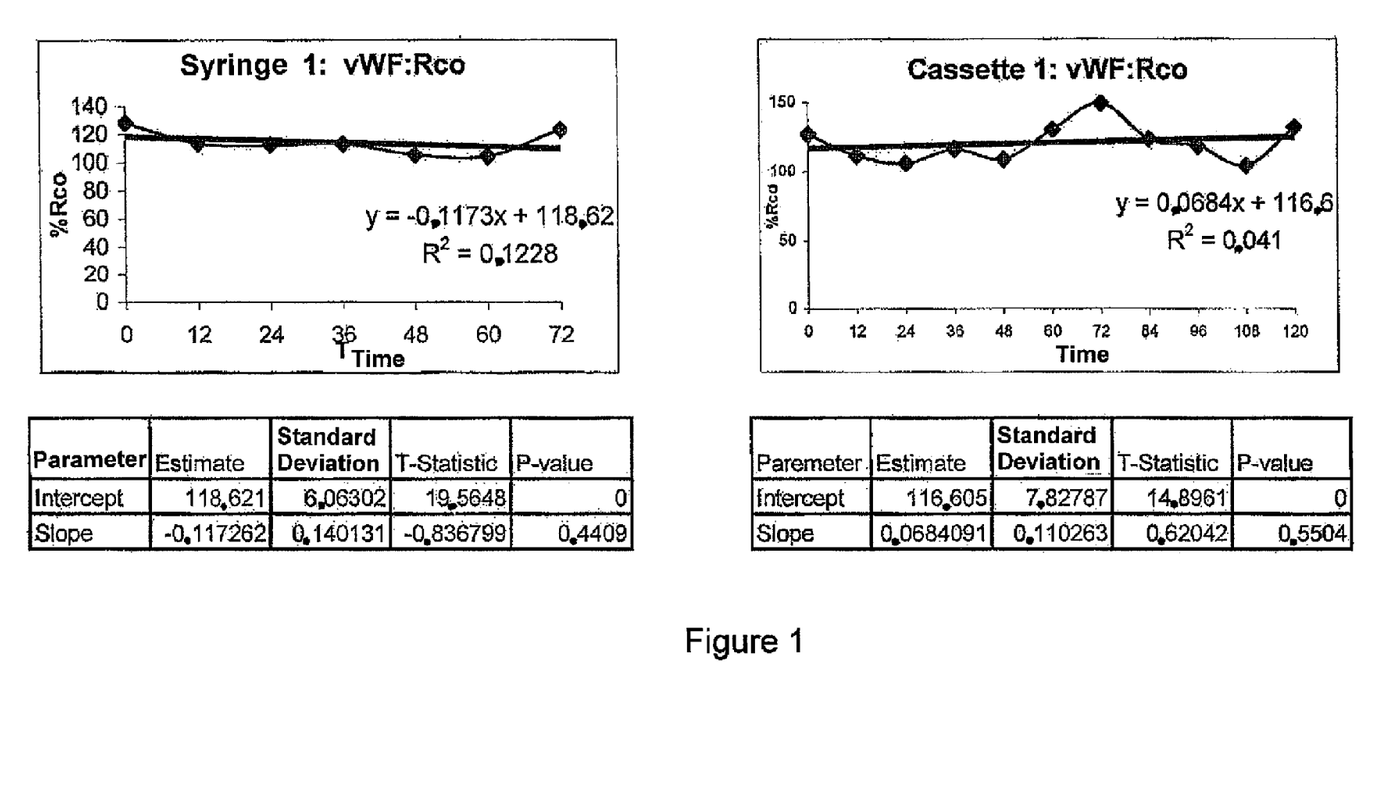
FIG. 1, FIG. 1 (Suite 1), and FIG. 1 (Suite 2) illustrate an assay for the stability of the RCo activity of the vWF concentrate.
Figure 2:
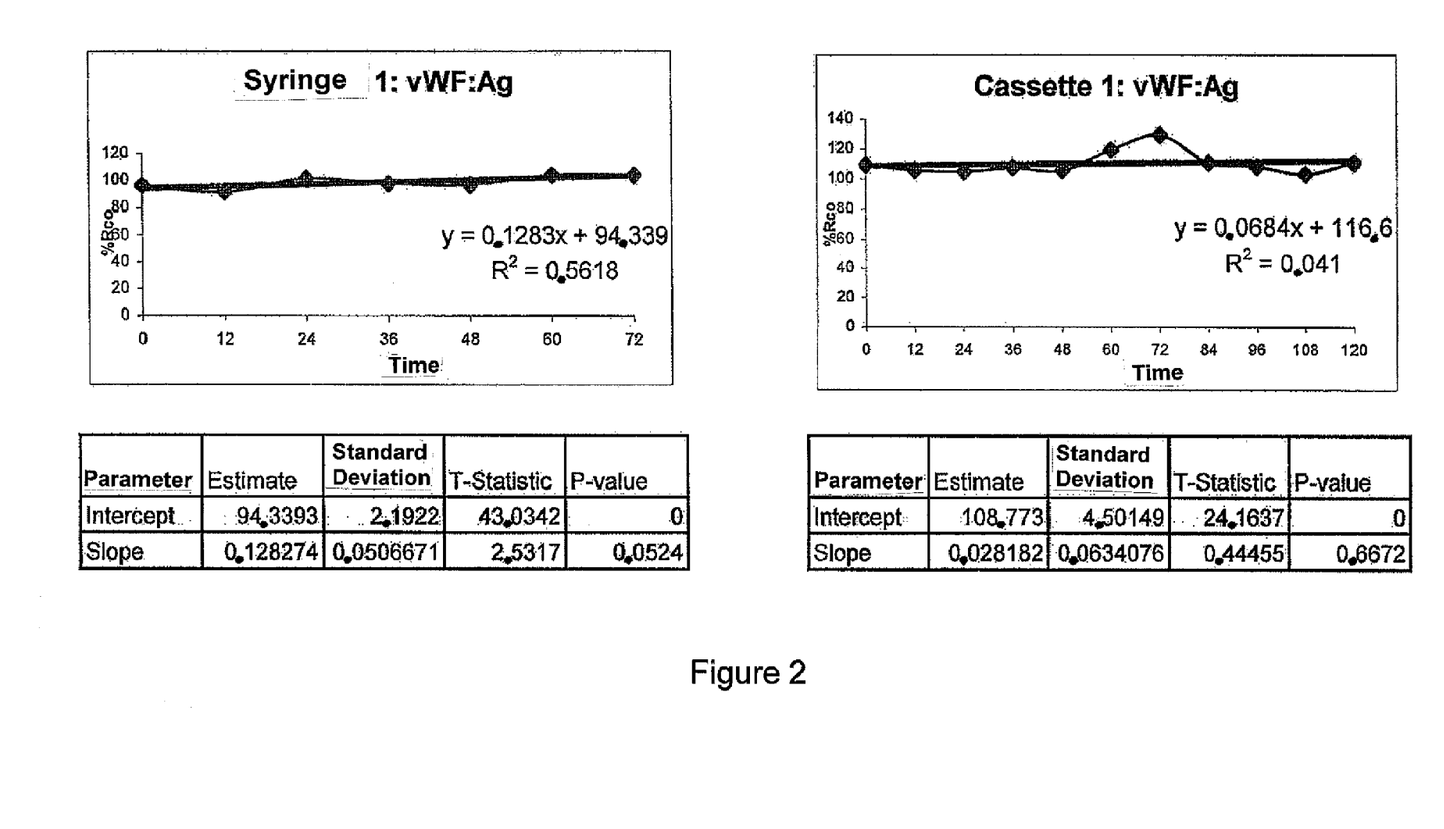
FIG. 2, FIG. 2 (Suite 1), and FIG. 2 (Suite 2) illustrate an assay for stability of the vWF antigen in the vWF concentrate.

The results are given in tables 2 and 3 for the raw data. Stability values vs. time depending on the ristocetin cofactor activity and on Willebrand antigens are illustrated on FIGS. 1 and 2.

TABLE 2

Results for the syringe assays (Raw data, Average values and Standard deviation)

| Batch | Syringe | Time (hour) | vWF:Rco (%) | vWF:Ag (%) |
|---|---|---|---|---|
| 1 | S1 | 0 | 128.2 | 96.3 |
|  | S1 | 12 | 113.5 | 92 |
|  | S1 | 24 | 112.3 | 101.4 |
|  | S1 | 36 | 113.4 | 97.8 |
|  | S1 | 48 | 105.6 | 97.1 |
|  | S1 | 60 | 104.5 | 104 |
|  | S1 | 72 | 123.3 | 104.1 |
| Average values (Standard deviation) |  |  | 114.4 (7.5) | 98.9 (4.5) |
| 2 | S2 | 0 | 132.1 | 103.4 |
|  | S2 | 12 | 122.3 | 101.8 |
|  | S2 | 24 | 125 | 105.1 |

TABLE 2-continued

Results for the syringe assays (Raw data, Average values and Standard deviation)

| Batch | Syringe | Time (hour) | vWF:Rco (%) | vWF:Ag (%) |
|---|---|---|---|---|
| | S2 | 36 | 133.4 | 100.3 |
| | S2 | 48 | 129.2 | 97.5 |
| | S2 | 60 | 137.7 | 105.7 |
| | S2 | 72 | 128.3 | 107 |
| Average values (Standard deviation) | | | 129.7 (4) | 103 (9.2) |
| 3 | S3 | 0 | 101.8 | 95.6 |
| | S3 | 12 | 101.3 | 97.6 |
| | S3 | 24 | 94.3 | 95 |
| | S3 | 36 | 91.2 | 100.3 |
| | S3 | 48 | 88.6 | 93.3 |
| | S3 | 60 | 108.3 | 90.4 |
| | S3 | 72 | 104 | 100 |
| Average values (Standard deviation) | | | 98.5 (7.3) | 96 (3.7) |

TABLE 3

Results for the cassette assays (Raw data, Average values and Standard deviation)

| Batch | Cassette | Time (hour) | vWF:Rco (%) | vWF:Ag (%) |
|---|---|---|---|---|
| 1 | K1 | 0 | 126.7 | 109.3 |
| | | 12 | 111.5 | 105.8 |
| | | 24 | 106.2 | 105 |
| | | 36 | 116.3 | 107.5 |
| | | 48 | 109.1 | 105.6 |
| | | 60 | 130.1 | 119.4 |
| | | 72 | 146.6 | 129.5 |
| | | 84 | 123.3 | 110.8 |
| | | 96 | 118.2 | 108.2 |
| | | 108 | 104.7 | 103.2 |
| | | 120 | 132.1 | 110.8 |
| Average values (Standard deviation) | | | 120.7 (11.71) | 110.5 (6.9) |
| 2 | K2 | 0 | 134.4 | 114.2 |
| | | 12 | 122.9 | 102.6 |
| | | 24 | 120.3 | 106.6 |
| | | 36 | 99.8 | 100.2 |
| | | 48 | 123.6 | 113.7 |
| | | 60 | 129.7 | 110.9 |
| | | 72 | 120.3 | 106.9 |
| | | 84 | 119.2 | 108.5 |
| | | 96 | 143.1 | 119.5 |
| | | 108 | 131.3 | 113 |
| | | 120 | 113.2 | 114.7 |
| Average values (Standard deviation) | | | 123.4 (9.2) | 110.4 (4.8) |
| 3 | K3 | 0 | 149.3 | 118.8 |
| | | 12 | 113.9 | 102.6 |
| | | 24 | 116.5 | 103.2 |
| | | 36 | 123.5 | 105.1 |
| | | 48 | 110.7 | 101 |
| | | 60 | 107.5 | 103.7 |
| | | 72 | 116.4 | 110.5 |
| | | 84 | 117.3 | 106.4 |
| | | 96 | 116.7 | 108.8 |
| | | 108 | 118.1 | 112.6 |
| | | 120 | 111.3 | 103.7 |
| Average values (Standard deviation) | | | 118.3 (9.4) | 107 (4.9) |

Tests on the regression slopes are not significantly different from zero with $\alpha=5\%$ and $p>0.05$ under the hypothesis of random and abnormal variations, this confirms the absence of a significant degradation of the studied parameters (vWF: RCo and vWF:Ag) within the time ranges (72 h and 120 h) and under the conditions of the assay.

Multimer Results

The results for the multimers are given in table 4.

TABLE 4

Results for the multimers

| Batch | Syringe/ Cassette | Time (hour) | Multimers 1.5% (% N) | | |
|---|---|---|---|---|---|
| | | | $\geq 15$ | $\geq 10$ | $\geq 5$ |
| 1 | S1 | 0 | 54 | 71 | 93 |
| | S1 | 72 | 43 | 63 | 91 |
| | K1 | 0 | 39 | 68 | 94 |
| | K1 | 60 | 31 | 58 | 90 |
| | K1 | 120 | 36 | 58 | 83 |
| 2 | S2 | 0 | 38 | 61 | 94 |
| | S2 | 72 | 29 | 47 | 76 |
| | K2 | T0 | 32 | 58 | 91 |
| | K2 | 60 | 30 | 56 | 90 |
| | K2 | 120 | 39 | 64 | 90 |
| 3 | S3 | 0 | 48 | 63 | 95 |
| | S3 | 72 | 36 | 55 | 89 |
| | K3 | 0 | 63 | 74 | 96 |
| | K3 | 60 | 61 | 75 | 95 |
| | K3 | 120 | 60 | 77 | 98 |

No significant difference is observed between the various multimers (high molecular weight, moderate and low molecular weights) throughout the study in the different containers (syringe and cassette).

Conclusion

The results of our study demonstrate the biological stability (qualitative and quantitative) of a vWF freeze-dried concentrate without ADAMTS13, reconstituted for the study period (for 72 h for the syringes and 120 h for the cassettes) under predetermined working conditions.

These results showed that it is possible to fractionate doses in syringes (for a paediatric administration for example); and to implement possible automated bolus administrations by means of an infusion pump or via a continuous infusion for von Willebrand disease (as is already practised for haemophilia).

The invention claimed is:

1. A method for reducing the ADAMTS13 amount in a solution derived from human vWF-containing plasma comprising an ion-exchange chromatography step on a large-pore, vinyl polymer-type resin bearing DEAE groups, performed in a buffer comprising trisodium citrate, sodium chloride, calcium chloride, glycine and lysine.

2. The method according to claim 1, wherein the ion-exchange chromatography support comprises a copolymer of oligoethylene glycol, glycidine methacrylate and pentaerythritol dimethacrylate on which DEAE groups are grafted.

3. The method according to claim 1, wherein the buffer for the chromatography comprises trisodium citrate 0.01 M, calcium chloride 0.001 M, glycine 0.12 M and lysine 0.016 M and sodium chloride varying from 0.11 M to 0.17 M.

4. The method according to claim 1, wherein the fraction which is adsorbed onto the chromatography support is eluted by increasing the sodium chloride concentration in the buffer to 0.14-0.17 M.

5. The method according to claim 1, wherein the pH value of the buffer does range from 6.9 to 7.1.

6. The method according to claim 1, wherein ADAMS 13 is removed by two successive chromatographic separation steps using said ion-exchange chromatography support and said buffer.

7. The method according to claim 1, wherein the reduction in the ADAMTS13 amount is higher than 200 times as compared to the ADAMTS13 amount comprised in the initial plasma.

8. The method according to claim 1, wherein the reduction in the ADAMTS13 amount is higher than 500 times as compared to the ADAMTS13 amount comprised in the initial plasma.

\* \* \* \* \*